*(12)* United States Patent
del Real Pena et al.

(10) Patent No.: US 11,479,397 B2
(45) Date of Patent: Oct. 25, 2022

(54) REUSABLE PACKAGING BAGS AND RELATED METHODS

(71) Applicant: Fresenius Medical Care Holdings, Inc., Waltham, MA (US)

(72) Inventors: Diego Suarez del Real Pena, Mission, TX (US); Jose Eduardo Pena Martinez, Reynosa (MX)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 17/109,129

(22) Filed: Dec. 1, 2020

(65) Prior Publication Data
US 2022/0169431 A1 Jun. 2, 2022

(51) Int. Cl.
*B65D 75/58* (2006.01)
*B65D 33/16* (2006.01)
*B65D 33/06* (2006.01)

(52) U.S. Cl.
CPC ....... *B65D 75/5833* (2013.01); *B65D 33/065* (2013.01); *B65D 33/1608* (2013.01)

(58) Field of Classification Search
CPC .............. B65D 75/8533; B65D 33/065; B65D 33/1608
USPC .......................................................... 383/8
See application file for complete search history.

(56) References Cited

U.S. PATENT DOCUMENTS

| 2,750,033 A | * | 6/1956 | Pickens | B65D 75/52 206/361 |
| 3,349,993 A | * | 10/1967 | Ells | B65D 75/585 383/203 |
| 3,352,411 A | * | 11/1967 | Schwarzkopf | A47F 13/085 206/493 |
| 3,729,361 A | * | 4/1973 | Westlake, Jr. | B65D 33/065 156/510 |
| 3,961,743 A | | 6/1976 | Hollowell | |
| 3,966,524 A | * | 6/1976 | Lehmacher | B29C 65/18 156/182 |
| 4,762,230 A | | 8/1988 | Croce | |
| 5,054,619 A | * | 10/1991 | Muckenfuhs | A61F 15/001 206/494 |
| 5,096,305 A | * | 3/1992 | Rimondi | B65D 33/065 383/37 |
| 2004/0136614 A1 | * | 7/2004 | Seidler | B65D 33/10 383/4 |
| 2006/0124494 A1 | * | 6/2006 | Clark, Jr. | B65D 75/5838 206/440 |
| 2008/0212903 A1 | * | 9/2008 | Germanow | B65F 1/0026 383/42 |
| 2011/0192754 A1 | | 8/2011 | Slominski et al. | |

(Continued)

*Primary Examiner* — Jes F Pascua
(74) *Attorney, Agent, or Firm* — FisherBroyles, LLP

(57) ABSTRACT

The disclosed packaging bags may include a flexible front sidewall and a flexible rear sidewall with at least a first closed edge, second closed edge, and third closed edge coupling the front sidewall to the rear sidewall. A perforation may be formed through the flexible front sidewall and the flexible rear sidewall along the first closed edge. The perforation may extend in a first segment from the first closed edge toward a central region of the packaging bag, in a second segment in a direction along the first closed edge, and in a third segment back to the first closed edge. The second segment may include at least one elongated ventilation slit. Various other related packaging bags and methods are also disclosed.

9 Claims, 7 Drawing Sheets

(56) References Cited

U.S. PATENT DOCUMENTS

2013/0272630 A1\* 10/2013 Thomas ............ B65D 75/5894
 383/201
2016/0001645 A1 1/2016 Ortmueller
2017/0007473 A1\* 1/2017 Germanow ........... A61F 13/551
2019/0300242 A1 10/2019 Lin et al.

\* cited by examiner

REUSABLE PACKAGING BAGS AND RELATED METHODS

BACKGROUND

Patients under home dialysis programs (e.g., continuous ambulatory peritoneal dialysis, automated peritoneal dialysis, home hemodialysis, etc.) may receive many supplies on a monthly basis, such as tubing sets, cleaning materials, receptacles, dialysate, medication, syringes, dialyzers, etc. Some of these supplies are typically sterilized and delivered to the patient in a sterile package. Ethylene oxide is a common sterilant used to sterilize such supplies because ethylene oxide is generally non-reactive and compatible with many different materials. Some packaging bags used to contain and deliver sterilized supplies include a ventilation slit for introducing ethylene oxide into the packaging bags for sterilization and/or for allowing ethylene oxide to exit out of the packaging bags.

The process of performing home dialysis often generates a significant amount of waste including used dialysis supplies, which must be discarded. Typically, patients or caregivers will collect and discard this waste in plastic bags or other trash receptacles, potentially creating additional waste.

DETAILED DESCRIPTION

The present disclosure provides detailed descriptions of reusable packaging bags and related methods. The disclosed reusable packaging bags may include a flexible front sidewall and a flexible rear sidewall with a perforation through the flexible front sidewall and the flexible rear sidewall. The perforation may define a removable portion. Handles may be positioned laterally adjacent to the perforation to remain after the removable portion is removed. The perforation may include at least one elongated ventilation slit (e.g., in addition to shorter slits and/or holes), such as to allow sterilant to vent out of the packaging bag. For example, the packaging bag may be configured to initially contain a first item (e.g., a medical item or device) that has been sterilized, such as by ethylene oxide, which may be introduced into and/or vented out of the packaging bag through the elongated ventilation slit. By configuring the perforation so handles remain after the removable portion is removed, the packaging bag may be reused, such as to hold another item or material (e.g., waste). The handles may also be tied together to secure the packaging bag closed.

Although not limited to such uses, the reusable packaging bags of the present disclosure may be useful for delivering supplies for home dialysis programs. The elongated ventilation slit may be used to sterilize and vent an item or material within the packaging bag. The user may remove the removable portion by tearing the packaging bag along the perforation, such as by holding the removable portion at the elongated ventilation slit and pulling the removable portion from the remaining portions of the packaging bag. After the sterilized item is removed from the packaging bag, the packaging bag may be reused, such as to hold and discard used supplies.

Figure 6:
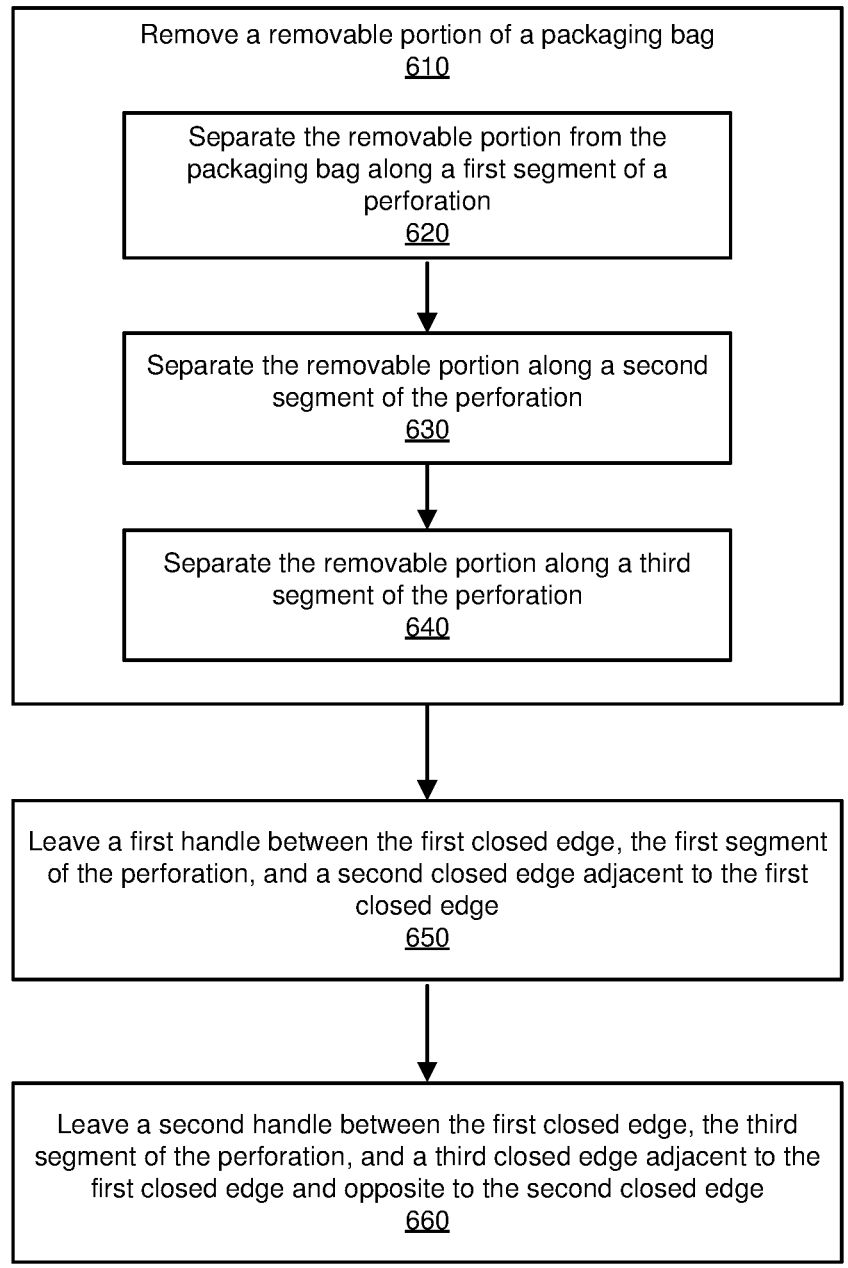
FIG. 6 is a flow diagram illustrating a method of using a packaging bag, according to at least one embodiment of the present disclosure.
Figure 7:
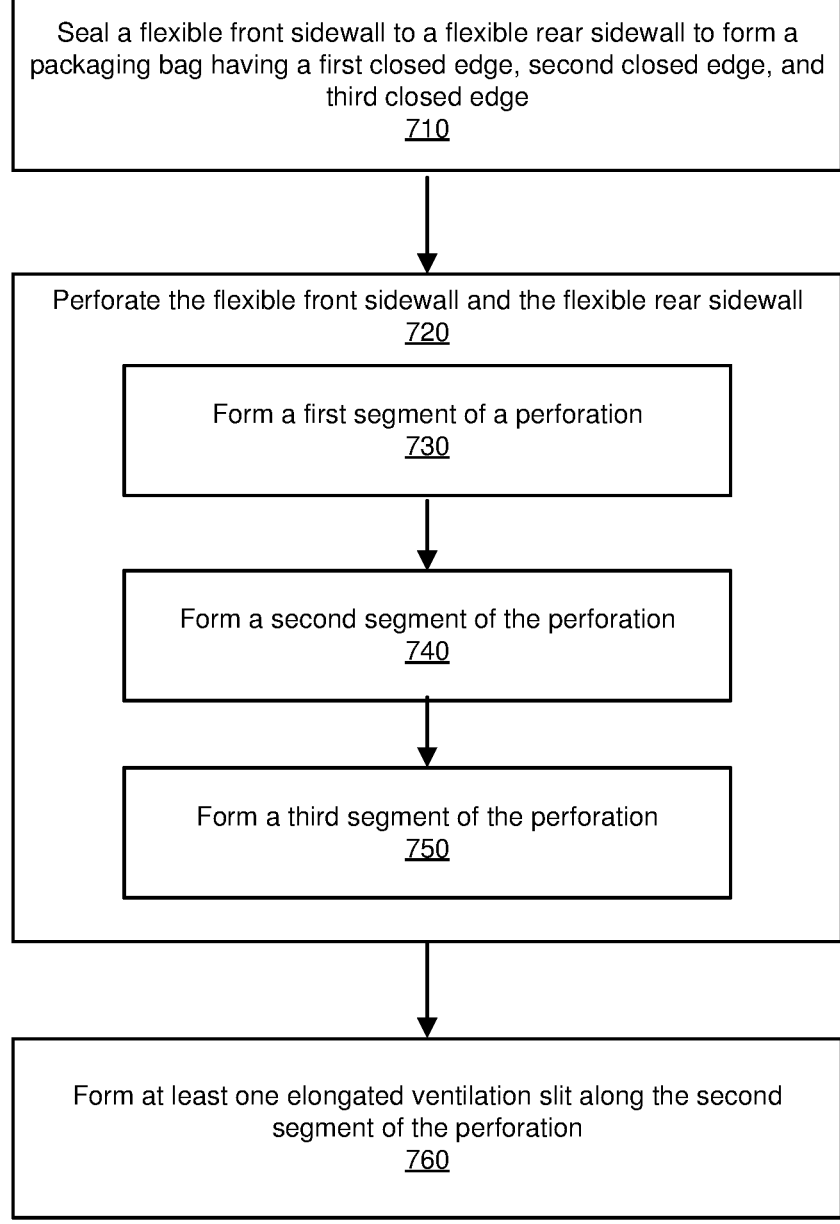
FIG. 7 is a flow diagram illustrating a method of forming a reusable packaging bag, according to at least one embodiment of the present disclosure.

The following will provide, with reference to FIGS. 1-5, detailed descriptions of reusable packaging bags and some of their uses. With reference to FIG. 6, the following will provide detailed descriptions of methods of using packaging bags. With reference to FIG. 7, the following will provide detailed descriptions of methods of forming reusable packaging bags.

Figure 1:
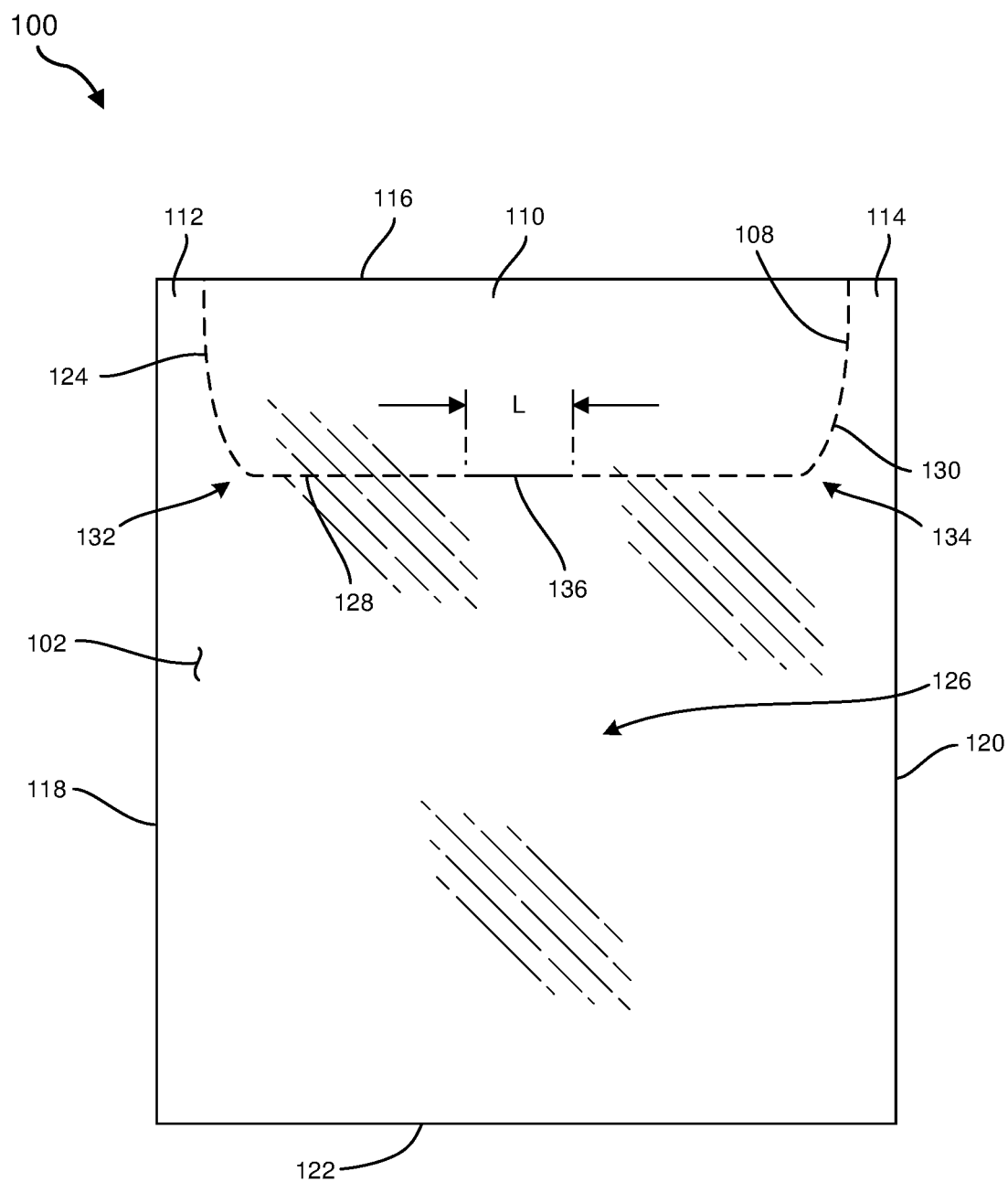
FIG. 1 is a plan view of a reusable packaging bag, according to at least one embodiment of the present disclosure.
Figure 2:
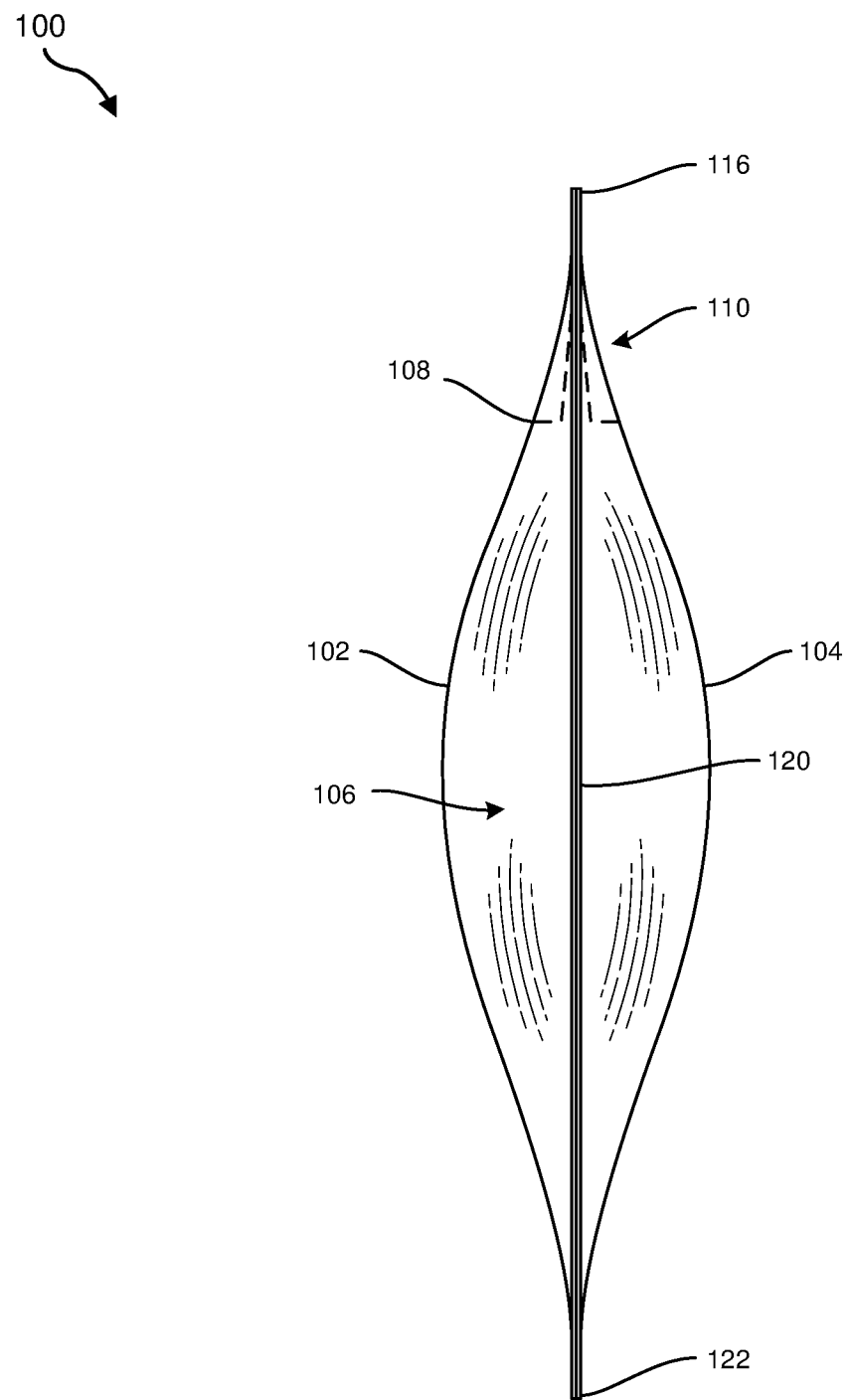
FIG. 2 is a side view of the reusable packaging bag of FIG. 1, according to at least one embodiment of the present disclosure.

FIG. 1 is a plan view of a reusable packaging bag 100, according to at least one embodiment of the present disclosure. FIG. 2 is a side view of the packaging bag 100 of FIG. 1. Referring to FIGS. 1 and 2, the packaging bag 100 may include a flexible front sidewall 102 and a flexible rear sidewall 104. An internal volume 106 of the packaging bag 100 may be defined between the flexible front sidewall 102 and the flexible rear sidewall 104. A perforation 108 may pass through the flexible front sidewall 102 and the flexible rear sidewall 104, forming a removable portion 110 of the packaging bag 100. A first handle 112 and a second handle 114 may be defined adjacent to the perforation 108. The first handle 112 and the second handle 114 may be configured to remain after the removable portion 110 is removed from the packaging bag 100 as a result of tearing along the perforation 108.

In some examples, relational terms, such as "first," "second," "front," "rear," etc., may be used for clarity and convenience in understanding the disclosure and accompanying drawings and do not connote or depend on any specific preference, orientation, or order, except where the context clearly indicates otherwise.

The flexible front sidewall 102 and the flexible rear sidewall 104 may be formed of a variety of materials. The material of the flexible front sidewall 102 and the flexible rear sidewall 104 may be selected based on materials and items to be contained by the packaging bag 100. For example, the material may be selected to be non-reactive with the materials and items to be contained, and/or may be selected based on mechanical properties (e.g., strength, flexibility, etc.) sufficient to contain the expected materials and items. By way of example and not limitation, the material of the flexible front sidewall 102 and the flexible rear sidewall 104 may be or include a polymer material, such as polyurethane, polyethylene, polypropylene, etc. For example, polyurethane may be suitable for use with storing medical equipment, and polyethylene and polypropylene may be suitable for use with storing food products. In some embodiments, the flexible front sidewall 102 and/or the flexible rear sidewall 104 may include a polymer material with a metallic coating (e.g., aluminum coating).

Edges of the flexible front sidewall 102 and of the flexible rear sidewall 104 may be closed, such as sealed (e.g., heat-sealed, adhered, etc.) to each other or formed integrally (e.g., formed as a single sheet and folded, extruded, etc.) with each other. For example, the packaging bag 100 may include a first closed edge 116, such as along a top of the packaging bag 100 from the perspectives of FIGS. 1 and 2. A second closed edge 118 may be adjacent to the first closed edge 116, such as along a left side of the packaging bag 100 from the perspective of FIG. 1. A third closed edge 120 may be adjacent to the first closed edge 116 on an opposite side of the packaging bag 100 from the second closed edge 118, such as along a right side of the packaging bag 100 from the perspective of FIG. 1. A fourth closed edge 122 may be on an opposite side of the packaging bag 100 from the first closed edge 116, such as along a bottom of the packaging bag 100 from the perspectives of FIGS. 1 and 2. In some examples, any of the closed edges 116, 118, 120, 122 may include a pleat (e.g., an inward fold), such as to increase a size of the internal volume 106.

The perforation 108 may include several segments that are located to define the removable portion 110. For example, the perforation 108 may include a first segment 124 that extends from the first closed edge 116 toward a central region 126 of the packaging bag 100. A second segment 128 of the perforation 108 may extend from the first segment 124 in a direction along (e.g., substantially parallel to) the first closed edge 116. A third segment 130 of the perforation 108 may extend from the second segment 128 back to the first closed edge 124.

The second segment 128 may extend between an end of the first segment 124 and an end of the third segment 130. The first segment 124 and the second segment 128 may intersect with each other at a first intersection 132. The third segment 130 and the second segment 128 may intersect with each other at a second intersection 134. Each of the first intersection 132 and the second intersection 134 may form a discrete angle, or the intersections 132, 134 may each form a smooth (e.g., curved, tangential) transition between the adjacent segments of the perforation 108. As shown in FIG. 1, in some embodiments, each of the first segment 124 and the third segment 130 may be curved (e.g., curved inward) and the second segment 128 may be substantially straight.

In some examples, the term "substantially" in reference to a given parameter, property, or condition, may refer to a degree that one skilled in the art would understand that the given parameter, property, or condition is met with a small degree of variance, such as within acceptable manufacturing tolerances. For example, a parameter that is substantially met may be at least about 90% met, at least about 95% met, at least about 99% met, or fully met.

Each of the segments 124, 128, 130 of the perforation 108 may include a series of slits and/or holes through the flexible front sidewall 102 and/or through the flexible rear sidewall 104, such that the removable portion 110 may be fully removable from the rest of the packaging bag 100 by tearing along the perforation 108. The second segment 128 may include at least one elongated ventilation slit 136, which may be collocated with (e.g., along a same line as) the perforation 108. The elongated ventilation slit 136 may be longer than other slits and/or holes of the perforation 108. The elongated ventilation slit 136 may be present in the flexible front sidewall 102, the flexible rear sidewall 104, or both the flexible front sidewall 102 and the flexible rear sidewall 104. The elongated ventilation slit 136 and the slits and/or holes of the perforation 108 may be formed by any suitable perforating technique, such as cutting, punching, puncturing, laser cutting, etc.

In additional embodiments, only one of the flexible front sidewall 102 or he flexible rear sidewall 102 may include the perforation 108. For example, the removable portion 110 may be or include a flap that folds back to allow access to the internal volume 106 of the packaging bag 100.

The elongated ventilation slit 136 may have a sufficient length to enable a fluid (e.g., a gas) to pass through the elongated ventilation slit 136 between the internal volume 106 of the packaging bag 100 and an exterior of the packaging bag 100. For example, the elongated ventilation slit 136 may have a length L of at least about 0.5 inch, such as 1.0 inch, 1.5 inches, 2.0 inches, or longer.

In some examples, the packaging bag 100 may be initially used to store an item, such as medical equipment, that has been sterilized with a sterilant, such as with ethylene oxide. The elongated ventilation slit 136 may be provided in the packaging bag 100 to allow ethylene oxide or another sterilant to be introduced into the packaging bag 100 to sterilize the item and/or to allow residual ethylene oxide or other sterilant to vent out of the packaging bag 100. The venting of the sterilant may be actively induced, such as by forcing a replacement gas (e.g., nitrogen, air, etc.) into the packaging bag 100 and/or applying a low external pressure to the packaging bag 100. Alternatively or additionally, the venting of the sterilant may be passive, such as by letting the packaging bag 100 containing the sterilized item to sit for a predetermined time that may be sufficient to allow a substantial portion of the sterilant to escape the packaging bag 100 through the elongated ventilation slit 136.

Figure 3:
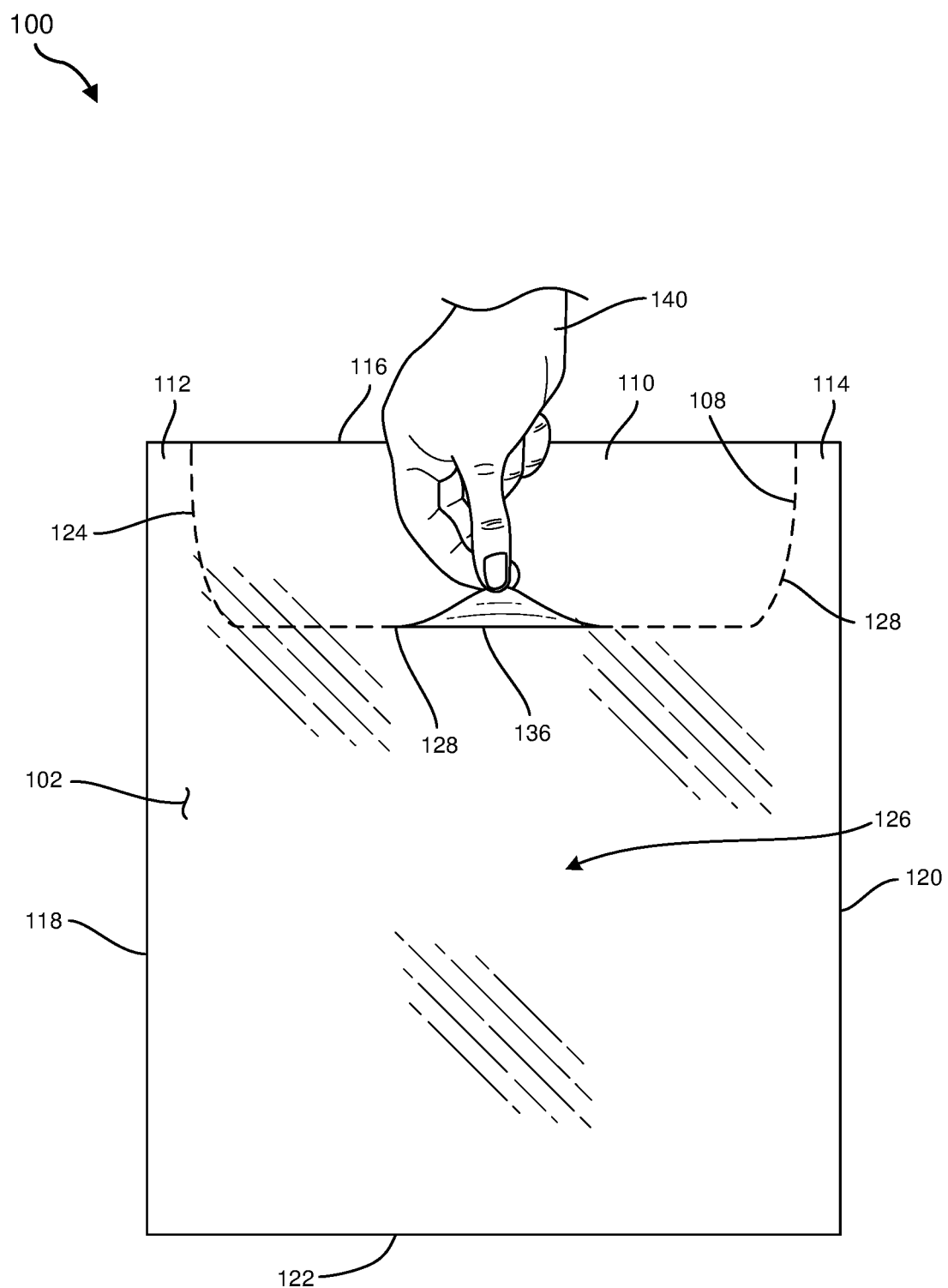
FIG. 3 is a plan view of the reusable packaging bag of FIGS. 1 and 2 in use, according to at least one embodiment of the present disclosure.
Figure 4:
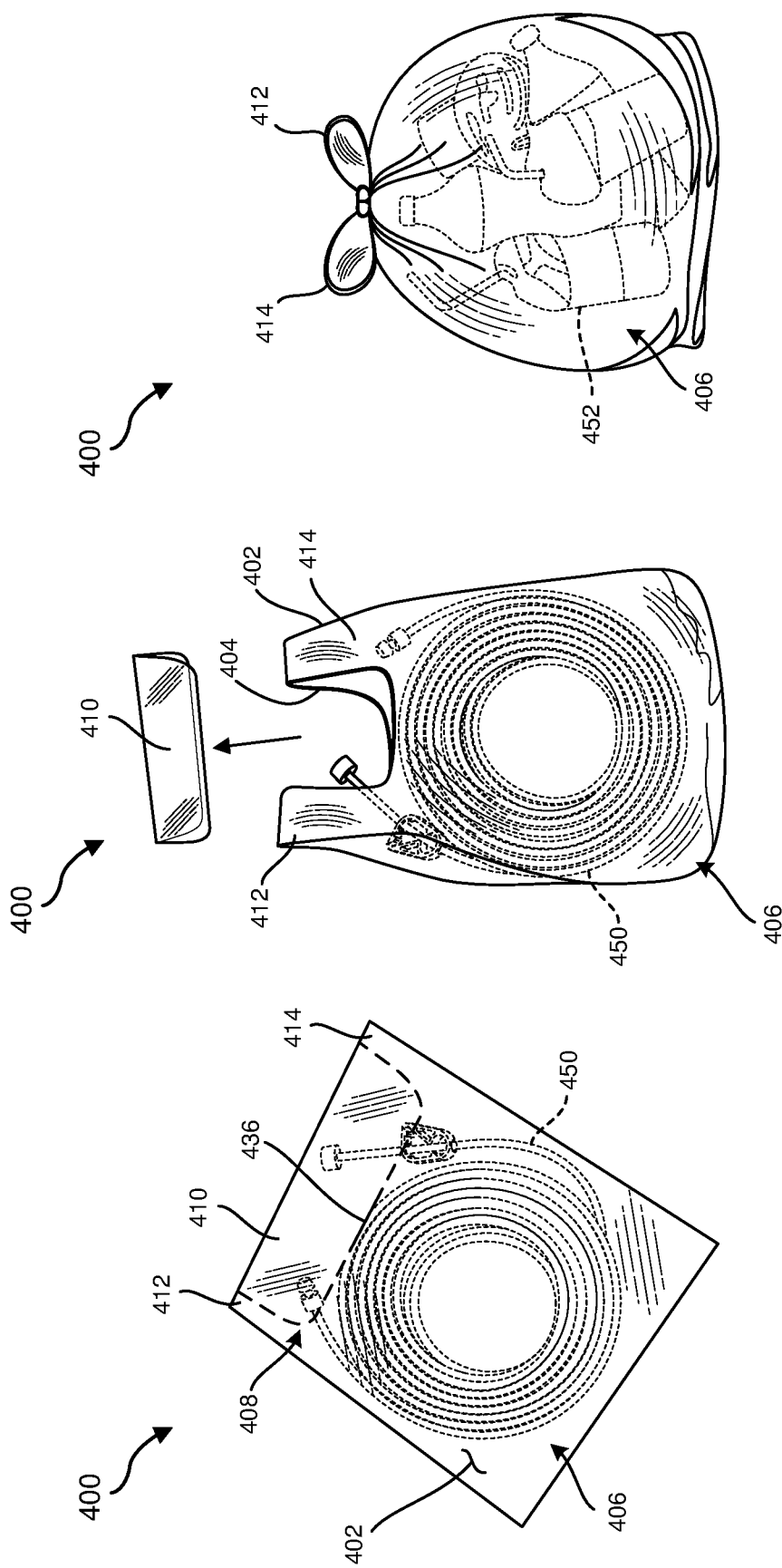
FIG. 4A is a perspective view of a reusable packaging bag holding a first item, according to at least one embodiment of the present disclosure.
FIG. 4B is a perspective view of the reusable packaging bag of FIG. 4A after a portion of the reusable packaging bag has been removed to form handles.
FIG. 4C is a perspective view of the reusable packaging bag of FIGS. 4A and 4B holding a second item, with the handles tied to each other.

FIG. 3 is a plan view of the reusable packaging bag 100 in use, according to at least one embodiment of the present disclosure. A user 140 may desire to open the packaging bag 100 to gain access to an item within the packaging bag 100. As illustrated in FIG. 3, the user 140 may grasp the removable portion 110 (e.g., the flexible front sidewall 102, the flexible rear sidewall 104, or both) adjacent to the elongated ventilation slit 136 and may tear the packaging bag 100 along the perforation 108 to remove the removable portion 110 from the remaining portions of the packaging bag 100. Thus, the elongated ventilation slit 136 may also (e.g., in addition to providing ventilation) function as a convenient place to grip the removable portion 110 for removing the removable portion 110.

Alternatively or additionally, the user 140 may tear along the perforation 108 by grasping the packaging bag 100 along the first closed edge 116 adjacent to the first segment 124 and/or adjacent to the third segment 130 of the perforation 108.

After the removable portion 110 is removed, the first handle 112 and the second handle 114 may remain. The handles 112, 114 may be used to hold the packaging bag 100 and/or to tie the packaging bag 100 closed.

FIG. 4A is a perspective view of a reusable packaging bag 400 holding at least one first item 450, according to at least one embodiment of the present disclosure. In some respects, the packaging bag 400 may be similar to the packaging bag 100 described above. For example, the packaging bag 400 may include a flexible front sidewall 402 and a flexible rear sidewall 404, with an internal volume 406 of the packaging bag 400 being defined between the flexible front sidewall 402 and the flexible rear sidewall 404. A perforation 408, which may include an elongated ventilation slit 436, may define a removable portion 410 of the packaging bag 400. A first handle 412 and a second handle 414 may be located laterally adjacent to the removable portion 410 and laterally outside the perforation 408.

FIG. 4B is a perspective view of the packaging bag 400 of FIG. 4A after the removable portion 410 of the packaging bag 400 has been removed to form the first and second handles 412, 414 and to open the packaging bag 400. FIG. 4C is a perspective view of the packaging bag 400 of FIGS. 4A and 4B holding at least one second item 452, with the first and second handles 412, 414 tied to each other.

Referring to FIG. 4A, the packaging bag 400 may initially be used for a first purpose, such as to contain the first item 450. The first item 450 may be any desired item or material that fits within the internal volume 406. By way of example and not limitation, the first item 450 may include medical equipment (e.g., a tubing set for hemodialysis, a tubing set for intravenous delivery of medication, an instrument for surgery, etc.), which may be sterilized. For example, the first item 450 may have been sterilized with a sterilant, such as ethylene oxide. The elongated ventilation slit 436 may be configured to allow at least some residual sterilant to exit out of the internal volume 406 of the packaging bag 400.

Referring to FIG. 4B, the packaging bag 400 may be opened by tearing along the perforation 408 (including along the elongated ventilation slit 436) to remove the removable portion 410. For example, a user may insert a finger through the elongated ventilation slit 436 to grasp the removable portion 410 and then tear the packaging bag 400 along the perforation 408, in the manner described above with reference to FIG. 3. Once the removable portion 410 is removed, the internal volume 406 may be accessed, such as to reach and remove the first item 450. The first handle 412 and the second handle 414 may remain after removal of the removable portion 410. The first handle 412 and/or the second handle 414 may be used to carry the packaging bag 400 and any item(s) or material(s) therein. At this point (e.g., after removal of the removable portion 410), the remaining portions of the packaging bag 400 may take the form of a so-called "T-shirt" bag.

With the removable portion 410 removed, the packaging bag 400 may be used for a second purpose, such as to contain the at least one second item 452 (see FIG. 4C). For example, the at least one second item 452 may include refuse, an item that the first item 450 replaces, the removable portion 410, and/or the first item 450 after use.

As shown in FIG. 4C, if desired, the packaging bag 400 may be secured in a closed position with the second item(s) 452 therein by tying the first handle 412 and the second handle 414 together.

Accordingly, packaging bags of the present disclosure may be reusable. As described above, a first use may include containing (e.g., storing, transporting, etc.) a first item or material, such as sterilized medical equipment. The elongated ventilation slit may be used to introduce and/or vent a sterilant. The perforation (including the elongated ventilation slit that may be collocated with perforation slits and/or holes) may be used to remove the removable portion, and the remaining packaging bag may include handles. A second use of the packaging bag may include containing (e.g., storing, transporting, etc.) a second item or material. In some examples, the handles may be tied together to secure the second item or material within the packaging bag.

Figure 5:
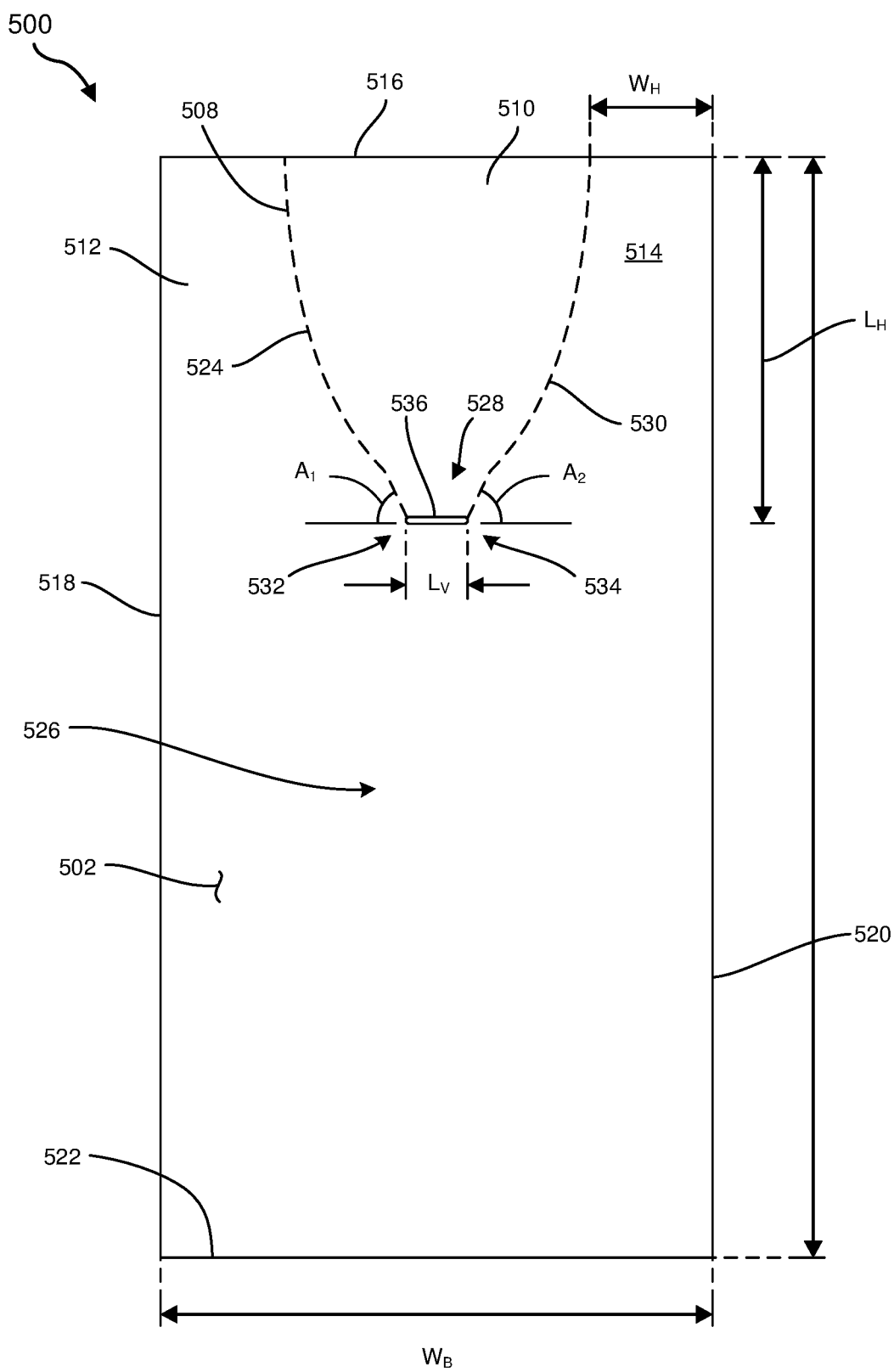
FIG. 5 is a plan view of a reusable packaging bag, according to at least one additional embodiment of the present disclosure.

FIG. 5 is a plan view of a reusable packaging bag 500, according to at least one additional embodiment of the present disclosure. In some respects, the packaging bag 500 may be similar to the packaging bags 100, 400 described above. For example, the packaging bag 500 may include a flexible front sidewall 502 and a flexible rear sidewall (not visible in the view of FIG. 5) that define an internal volume therebetween. A perforation 508 may define a removable portion 510 of the packaging bag 500. A first handle 512 and a second handle 514 may be located on opposing sides of the removable portion 510, laterally adjacent to the perforation 508.

The packaging bag 500 may include a first closed edge 516, a second closed edge 518 adjacent to the first closed edge 516, and a third closed edge 520 adjacent to the first closed edge 516 opposite the second closed edge 518. A fourth closed edge 522 may extend from the second closed edge 518 to the third closed edge 520 opposite the first closed edge 516.

The perforation 508 of the packaging bag 500 may include several perforation segments. For example, the perforation 508 may include a first segment 524 extending from the first closed edge 516 along the first handle 512 toward a central region 526 of the packaging bag 500. A second segment 528 may extend from the first segment 524 in a direction along (e.g., substantially parallel to) the first closed edge 516. A third segment 530 of the perforation 508 may extend from the second segment 528 back to the first closed edge 524. The first segment 524 and the second segment 528 may intersect with each other at a first intersection 532, and the second segment 528 and the third segment 530 may intersect with each other at a second intersection 534.

The packaging bag 500 of FIG. 5 has been labeled with various dimensions. These dimensions are provided by way of example and not limitation. Packaging bags according to the present disclosure may have a variety of designs (e.g., shapes, sizes, dimensions, relative placement of perforations and elongated ventilation slits, length of perforation segments, angle of perforation segments, shape of perforation segments, etc.). Although the packaging bag 500 is shown as generally rectangular, other shapes are also included in the present disclosure (e.g., trapezoidal, triangular, curved edges, etc.).

As shown in FIG. 5, the packaging bag 500 may have a length $L_B$ between the first closed edge 516 and the fourth closed edge 522 and a width $W_B$ between the second closed edge 518 and the third closed edge 520. In a rectangular configuration, the length $L_B$ may be a length of each of the second closed edge 518 and the third closed edge 520 (e.g., the second and third closed edges 518, 520 may have a common length $L_B$). Similarly, the width $W_B$ may be a length of each of the first closed edge 516 and of the fourth closed edge 522 (e.g., the first and fourth closed edges 516, 522 may have a common length $W_B$). The length $L_B$ and the width $W_B$ of the packaging bag 500 may be selected based on a size, shape, weight, or other characteristic of a material or item to be contained within the packaging bag 500. Although FIG. 5 illustrates the packaging bag 500 with the length $L_B$ greater than the width $W_B$, in additional embodiments the width $W_B$ may be greater than the length $L_B$.

A handle length $L_H$ may be defined to extend from the first closed edge 516 along the second and/or third closed edge 518, 520 to the second segment 528 (e.g., to the elongated ventilation slit 536) of the perforation 508. The handle length $L_H$ may identify a location of the elongated ventilation slit 536 relative to the first closed edge 516. By way of example and not limitation, the handle length $L_H$ may be between about one fifth and about one half of the length $L_B$ of the packaging bag 500. For example, the handle length $L_H$ may be about one third of the length $L_B$ of the packaging bag 500. Stated differently, the second segment 528 of the perforation 508 may be located between about one fifth and about one half (such as about one third) of the length $L_B$ from the first closed edge 516. In some examples, the handle length $L_H$ may be at least about 3.0 inches, such as between about 3.0 inches and about 8.0 inches.

A handle width $W_H$ may be defined as a lateral width of each of the handles 512, 514 between the perforation 508 and the respective second closed edge 518 or third closed edge 520. In some examples, the handle width $W_H$ may be at least about 1.5 inches, such as between about 1.5 inches and about 4.0 inches.

The first intersection 532 may have a first angle $A_1$, which may be measured from the second segment 528 toward the first closed edge 516 (e.g., from an imaginary line extending outward from the second segment 528 toward the first closed edge 516) to the first segment 524. Likewise, the second intersection 534 may have a second angle $A_2$, which may be measured from the second segment 528 toward the third closed edge 520 (e.g., from an imaginary line extending outward from the second segment 528 toward the third closed edge 520) to the third segment 530. In some embodiments, each of the first and second angles $A_1$, $A_2$ may be at least about 45 degrees, such as between about 60 degrees and about 90 degrees. The first and second angles $A_1$, $A_2$ of the respective first and second intersections 532, 534 may be configured to facilitate tearing the packaging bag 500 along the perforation 508.

The elongated ventilation slit 536 may have a vent length $L_V$ that is long enough to allow ventilation into and/or out of the internal volume of the packaging bag 500. The vent length $L_V$ may also be long enough to enable a user to grasp the removable portion 510 by inserting a finger through the elongated ventilation slit 536, to facilitate tearing along the perforation 508 and removal of the removable portion. By way of example and not limitation, the vent length $L_V$ may be at least about 0.5 inch, such as about 1.0 inch, about 1.5 inches, about 2.0 inches, or greater than about 2.0 inches.

As illustrated in FIG. 5, in some examples, the second segment 528 may be entirely defined by the elongated ventilation slit 536. In additional embodiments, the second segment 528 may include the elongated ventilation slit 536 and one or more shorter slits and/or holes (e.g., as illustrated in FIG. 1).

FIG. 6 is a flow diagram illustrating a method 600 of using a packaging bag, according to at least one embodiment of the present disclosure. At operation 610, a removable portion of a packaging bag may be removed. Operation 610 may be performed in a variety of ways. For example, operation 610 may include operations 620, 630, and 640, as described below.

At operation 620, the removable portion may be separated from remaining portions of the packaging bag along a first segment of a perforation. Operation 620 may be performed in a variety of ways. For example, the first segment of the perforation may extend from a first closed edge of the packaging bag toward a central region of the packaging bag. The separation of the packaging bag along first segment of the perforation may be performed by grasping the removable portion of the packaging bag along the first closed edge and tearing the packaging bag toward the central region of the packaging bag along the first segment. Alternatively, the separation may be performed by grasping the removable portion of the packaging bag in a different location, such as near the inner end of the first segment (e.g., the end of the first segment closest to the central region of the packaging bag) and tearing the packaging bag toward the first closed edge of the packaging bag. Slits and/or holes defining the first segment of the perforation may act as a guide for separating the removable portion of the packaging bag from the remaining portions of the packaging bag.

At operation 630, the removable portion may be separated from remaining portions of the packaging bag along a second segment of the perforation. Operation 630 may be performed in a variety of ways. For example, the second segment may extend along (e.g., substantially parallel to) the first closed edge of the packaging bag. The second segment may include an elongated ventilation slit. In some embodiments, the second segment may also include one or more slits and/or holes in addition to the elongated ventilation slit. The removable portion may be separated from the remaining portion of the packaging bag along the second segment by tearing the packaging bag along the second segment. For example, a user may grasp the removable portion adjacent to the elongated ventilation slit and my pull the removable portion away from the remaining portions of the packaging bag. Alternatively, the user may grasp the removable portion near an end of the second segment of the perforation, such as near the first segment of the perforation and/or near an end of the second segment opposite the first segment.

At operation 640, the removable portion may be separated from remaining portions of the packaging bag along a third segment of the perforation. Operation 640 may be performed in a variety of ways. For example, the third segment of the perforation may extend from the first closed edge of the packaging bag toward the central region of the packaging bag. The separation of the packaging bag along third segment of the perforation may be performed by grasping the removable portion of the packaging bag along the first closed edge and tearing the packaging bag toward the central region of the packaging bag along the third segment. Alternatively, the separation may be performed by grasping the removable portion of the packaging bag in a different location, such as near the inner end of the third segment (e.g., the end of the third segment closest to the central region of the packaging bag) and tearing the packaging bag toward the first closed edge of the packaging bag. Slits and/or holes defining the third segment of the perforation may act as a guide for separating the removable portion of the packaging bag from the remaining portions of the packaging bag.

Operations 620, 630, and 640 may be performed in any order and/or simultaneously. For example, the user may initially grasp the removable portion of the packaging bag adjacent to the elongated ventilation slit of the second segment and may start the removal process by performing operation 630 and tearing the packaging bag along the second segment. As the user continues pulling on the removable portion, operations 620 and 640 may be simultaneously performed and the packaging bag may be torn along both of the first segment and the third segment at the same time.

At operation 650, and as a result of performing operation 610, a first handle may be left between the first closed edge, the first segment of the perforation, and a second closed edge of the packaging bag adjacent to the first closed edge. As described above with reference to FIGS. 1-5, the packaging bag may include a first handle laterally adjacent to the removable portion. After the removable portion is removed, the first handle may remain. The first handle may be used to hang the remaining portions of the packaging bag and/or to tie the packaging bag closed.

At operation 660, and as a result of performing operation 610, a second handle may be left between the first closed edge, the third segment of the perforation, and a third closed edge of the packaging bag adjacent to the first closed edge and opposite the second closed edge. As described above with reference to FIGS. 1-5, the packaging bag may include a second handle laterally adjacent to the removable portion and opposite the first handle. After the removable portion is removed, the second handle may remain. The second handle may be used to hang the remaining portions of the packaging bag and/or to tie the packaging bag closed.

In some examples, prior to performing operation 610, a first item (e.g., medical equipment) may be stored in the packaging bag. The first item may have been cleaned by a sterilant, such as ethylene oxide. Residual sterilant may be allowed to or forced to vent out of the packaging bag through the elongated ventilation slit. After performing operations 610, 650, and 660, a different second item may be stored in the packaging bag. The second item may be, for example, an item that the first item replaces and/or waste material. In some embodiments, the second item may be secured in the packaging bag by tying the first handle and the second handle to each other.

FIG. 7 is a flow diagram illustrating a method 700 of forming a reusable packaging bag, according to at least one embodiment of the present disclosure. At operation 710, a flexible front sidewall may be sealed to a flexible rear sidewall to form the packaging bag. The packaging bag may have at least a first closed edge, a second closed edge, and a third closed edge. Operation 710 may be performed in a variety of ways. For example, at least one of the first, second, and/or third closed edges may be sealed by cutting with a hot knife, punch, or scissors, by adhering the flexible front sidewall and the flexible rear sidewall to each other with an adhesive, and/or crimping the flexible front sidewall and the flexible rear sidewall to each other.

At operation 720, the flexible front sidewall and the flexible rear sidewall may be perforated to define a removable portion of the packaging bag. Operation 720 may be performed in a variety of ways. For example, operation 720 may include operations 730, 740, and 750, as described below.

At operation 730, a first segment of a perforation may be formed. Operation 730 may be performed in a variety of ways. For example, the first segment may include slits and/or holes that extend in a line and/or curve from the first closed edge toward a central region of the packaging bag. The slits and/or holes may be formed by cutting, punching, puncturing, laser cutting, etc., the flexible front sidewall and the flexible rear sidewall.

At operation 740, a second segment of the perforation may be formed. Operation 740 may be performed in a variety of ways. For example, the second segment may include slits and/or holes that extend along (e.g., substantially parallel to) the first closed edge of the packaging bag. The slits and/or holes may be formed by cutting, punching, puncturing, laser cutting, etc., the flexible front sidewall and the flexible rear sidewall.

At operation 750, a third segment of the perforation may be formed. Operation 750 may be performed in a variety of ways. For example, the third segment may include slits and/or holes that extend in a line and/or curve from the first closed edge toward a central region of the packaging bag. The slits and/or holes may be formed by cutting, punching, puncturing, laser cutting, etc., the flexible front sidewall and the flexible rear sidewall. The third segment may be on an opposite side of the second segment relative to the first segment.

The operations 730, 740, and 750 may be performed sequentially or simultaneously. For example, all three segments of the perforation may be punched with a single die in one operation. In additional examples, the flexible front sidewall and the flexible rear sidewall may be cut along the perforation from one end to an opposite end of the perforation.

At operation 760, at least one elongated ventilation slit may be formed along the second segment of the perforation. Operation 760 may be performed in a variety of ways. For example, the at least one elongated ventilation slit may be formed in the flexible front sidewall, in the flexible rear sidewall, or in both of the flexible front sidewall and flexible rear sidewall. The at least one elongated ventilation slit may be formed by cutting, punching, puncturing, laser cutting, etc., the flexible front sidewall and/or the flexible rear sidewall. The at least one elongated ventilation slit may be formed prior to, simultaneous with, or after forming the remainder of the perforation.

Accordingly, the present disclosure includes reusable packaging bags and related methods that may improve upon conventional packaging bags, such as packaging bags used for the sterilization of and containing medical equipment. By providing a perforation in a configuration to leave handles, packaging bags according to the present disclosure may be reused after a first item is removed from the packaging bag, such as to hold a second item or material. The packaging bag may be tied closed with the handles that remain after tearing along the perforation and removing a removable portion. In addition, an elongated ventilation slit that is collocated along the perforation may be used to vent a fluid from the internal volume of the packaging bag, such as a residual sterilant used to sterilize the first item held within the packaging bag.

The following example embodiments are also included in the present disclosure.

Example 1: A reusable packaging bag, which may include: a flexible front sidewall; a flexible rear sidewall, wherein an internal volume of the packaging bag is defined between the flexible front sidewall and the flexible rear sidewall; at least a first closed edge, second closed edge, and third closed edge coupling the front sidewall to the rear sidewall; and a perforation through the flexible front sidewall and the flexible rear sidewall along the first closed edge, wherein the perforation extends in a first segment from the first closed edge toward a central region of the packaging bag, in a second segment in a direction along the first closed edge, and in a third segment back to the first closed edge, wherein the second segment includes at least one elongated ventilation slit.

Example 2: The reusable packaging bag of Example 1, wherein: the first segment of the perforation is located in a first distance from the second closed edge to define a first handle between the first segment and the second closed edge; and the third segment of the perforation is located a second distance from the third closed edge to define a second handle between the third segment and the third closed edge.

Example 3: The reusable packaging bag of Example 2, wherein each of the first distance and the second distance is at least about 1.5 inches.

Example 4: The reusable packaging bag of Example 3 or Example 3, wherein each of the first handle and the second handle has a length of at least about 3 inches.

Example 5: The reusable packaging bag of any of Examples 1 through 4, wherein each of the first segment and the third segment of the perforation is curved.

Example 6: The reusable packaging bag of any of Examples 1 through 5, wherein the second segment of the perforation is substantially straight.

Example 7: The reusable packaging bag of any of Examples 1 through 6, wherein the at least one elongated ventilation slit has a length of at least about 0.5 inch.

Example 8: The reusable packaging bag of any of Examples 1 through 7, wherein the second closed edge and the third closed edge each have a common length that extends away from the first closed edge, wherein the second segment of the perforation is located between about one fifth and about one half of the common length from the first closed edge.

Example 9: The reusable packaging bag of Example 8, wherein the second segment of the perforation is located about one third of the common length from the first closed edge.

Example 10: The reusable packaging bag of any of Examples 1 through 9, wherein at least a portion of the second segment of the perforation is parallel to the first closed edge.

Example 11: The reusable packaging bag of any of Examples 1 through 10, wherein a portion of the flexible front sidewall and of the flexible rear sidewall between the first closed edge, the first segment, the second segment, and the third segment is removable by tearing along the perforation.

Example 12: The reusable packaging bag of any of Examples 1 through 11, wherein: the first segment and the second segment intersect at a first intersection; and the third segment and the second segment intersect at a second intersection.

Example 13: The reusable packaging bag of Example 12, wherein: the first intersection has a first angle measured from the second segment toward the first closed edge to the first segment, and the first angle is at least about 45 degrees; and the second intersection ahs a second angle measured from the second segment toward the first closed edge to the third segment, and the second angle is at least about 45 degrees.

Example 14: The reusable packaging bag of Example 13, wherein each of the first angle and the second angle is between about 60 degrees and about 90 degrees.

Example 15: The reusable packaging bag of any of Examples 1 through 14, wherein each of the flexible front sidewall and the flexible rear sidewall includes a polymer material.

Example 16: A method of using a packaging bag, which may include: removing a removable portion of the packaging bag, including: separating the removable portion from the packaging bag along a first segment of a perforation that extends from a first closed edge toward a central region of the packaging bag; separating the removable portion along a second segment of the perforation including along an elongated ventilation slit; and separating the removable portion along a third segment of the perforation that extends from the second segment to the first closed edge; leaving a first handle between the first closed edge and a second closed edge that is adjacent to the first closed edge; and leaving a second handle between the first closed edge and a third closed edge that is adjacent to the first closed edge that is opposite the second closed edge.

Example 17: The method of Example 16, which may further include: prior to removing the removable portion of the packaging bag, storing a first item in the packaging bag; and after removing the removable portion of the packaging bag, storing a different second item in the packaging bag.

Example 18: The method of Example 17, wherein storing the first item in the packaging bag includes storing an item that has been sterilized with ethylene oxide.

Example 19: A method of forming a reusable packaging bag, which may include: sealing a flexible front sidewall to a flexible rear sidewall to form a packaging bag having at least a first closed edge, a second closed edge, and a third closed edge; perforating the flexible front sidewall and the flexible rear sidewall, including: forming a first segment of a perforation from the first closed edge toward a central region of the packaging bag; forming a second segment of the perforation in a direction substantially parallel to the first closed edge; and forming a third segment of the perforation from the second segment to the first closed edge; and forming at least one elongated ventilation slit along the second segment of the perforation.

Example 20: The method of Example 19, wherein forming the at least one elongated ventilation slit includes forming the at least one elongated ventilation slit through only the flexible front sidewall.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

The preceding description has been provided to enable others skilled in the art to best utilize various aspects of the example embodiments disclosed herein. This example description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A method of using a packaging bag, the method comprising:
    storing a first item that has been sterilized with ethylene oxide in a packaging bag;
    removing a removable portion of the packaging bag to access the first item, comprising:

separating the removable portion from the packaging bag along a first segment of a perforation that extends from a first closed edge toward a central region of the packaging bag;

separating the removable portion along a second segment of the perforation including along an elongated ventilation slit; and separating the removable portion along a third segment of the perforation that extends from the second segment to the first closed edge;

leaving a first handle between the first closed edge and a second closed edge that is adjacent to the first closed edge;

leaving a second handle between the first closed edge and a third closed edge that is adjacent to the first closed edge and that is opposite the second closed edge; and after removing the removable portion of the packaging bag, storing a different second item in the packaging bag.

2. The method of claim 1, wherein at least a portion of the second segment of the perforation is parallel to the first closed edge.

3. The method of claim 1, wherein:
the first handle has a width of at least about 1.5 inches between the second closed edge and the first segment of the perforation; and
the first handle has a width of at least about 1.5 inches between the third closed edge and the third segment of the perforation.

4. The method of claim 1, wherein:
the first handle has a length of at least about 3 inches; and
the second handle has a length of at least about 3 inches.

5. The method of claim 1, wherein:
the first segment of the perforation is curved; and
the third segment of the perforation is curved.

6. The method of claim 1, wherein the elongated ventilation slit has a length of at least about 0.5 inch.

7. The method of claim 1, wherein storing the different second item in the packaging bag comprises storing a refuse item in the packaging bag.

8. The method of claim 1, wherein storing a first item that has been sterilized with ethylene oxide in the packaging bag comprises storing a medical item in the packaging bag.

9. The method of claim 8, wherein storing the different second item in the packaging bag comprises storing a second item that the first item replaces.

* * * * *